United States Patent [19]

Rose et al.

[11] Patent Number: 4,920,989

[45] Date of Patent: May 1, 1990

[54] METHOD AND APPARATUS FOR AIDING IN THE REDUCTION OF INCIDENCE OF TOBACCO SMOKING

[75] Inventors: Jed E. Rose, Venice; Murray E. Jarvik, Santa Monica; Karce D. Rose, Healdsburg, all of Calif.

[73] Assignee: Regents of the University of California, Alameda, Calif.

[21] Appl. No.: 157,536

[22] Filed: Feb. 19, 1988

Related U.S. Application Data

[62] Division of Ser. No. 727,525, Apr. 25, 1985.

[51] Int. Cl.$^5$ .................. A24F 47/00; A61K 9/00
[52] U.S. Cl. .................................................. 131/270
[58] Field of Search ............... 514/314; 604/896, 897, 604/46; 131/270

[56] References Cited

U.S. PATENT DOCUMENTS

| 4,473,083 | 9/1984 | Maganias | 604/46 |
| 4,579,858 | 4/1986 | Ferno et al. | 131/270 |
| 4,597,961 | 7/1986 | Etscorn | 514/314 |
| 4,635,651 | 1/1987 | Jacobs | 131/220 |

FOREIGN PATENT DOCUMENTS

0930668 7/1973 Canada .................... 604/897

OTHER PUBLICATIONS

*Tobacco Alkaloids and Related Compounds* edited by Von Euler, pp. 3-13, A Pergamon Press Book, 1965.
"Bronchial Effects of Aerosolized Δ9-Tetrahydroconnobol in Healthy and Asthmatic Subjects" by Tasbin et al., American Review of Respiratory Disease, vol. 115, 1977.
"Drug Permeation through Human Skin: Theory and In Vitro Experimental Measurement" by Chandrasekaran et al., AICHE (vol. 21, No. 5), Sep. 1975, pp. 985-993.

Primary Examiner—V. Millin
Assistant Examiner—J. L. Doyle
Attorney, Agent, or Firm—Robert J. Schaap

[57] ABSTRACT

A method of aiding in the reduction of incidence of tobacco smoking. The method comprises applying a patch containing nicotine to the skin of a person with whom smoking reduction is desired and allowing the nicotine to transdermally migrate into the person's bloodstream to achieve a desired systemic nicotine level. The method also comprises the simultaneous administration of a nicotine containing aerosol spray to the oral cavity of the user in order to provide the desired sensations in the respiratory tract to which the user is accustomed from normal tobacco smoke. A combination of the spray and transdermal patch is also provided such that an occlusive patch is applied to the skin of the person with whom smoking reduction is desired and the nicotine containing aerosol spray is delivered to the oral cavity simultaneously with the application of the nicotine from the patch.

29 Claims, 3 Drawing Sheets

METHOD AND APPARATUS FOR AIDING IN THE REDUCTION OF INCIDENCE OF TOBACCO SMOKING

GOVERNMENT RIGHTS

This invention was made with U.S. Government support under Grant No. RR5756 awarded by the Department of Health and Human Services and under Grant No. 5 RO1 DA02665-04 awarded by the Department of Health and Human Services and the Medical Research Service of the Veterans Administration. The Government has certain rights in this invention.

RELATED APPLICATIONS

This application is a divisional application of U.S. patent application Ser. No. 727,525, filed Apr. 25, 1985, for "Method and Apparatus for Aiding in the Reduction of the Incidence of Tobacco Smoking", and is related to this aforesaid divisional application; and this present application is also related to U.S. patent application Ser. No. 157,948 filed Feb. 19, 1988 and which is also a division of the parent patent application Ser. No. 727,525, filed Apr. 25, 1985, for "Method and Apparatus for Aiding in the Reduction of the Incidence of Tobacco Smoking".

BACKGROUND OF THE INVENTION

1. Field of the Invention

This invention relates in general to certain new and useful improvements in method and apparatus for aiding in the reduction of the incidence of smoking, and more particularly, to a method and an apparatus which enables either the transdermal application of nicotine, or the oral administration of nicotine, or both in combination, to reduce the incidence of tobacco smoking.

2. Brief Description of the Prior Art

In recent years, with the recognition of the harmful effects of tobacco smoking, there have been numerous campaigns and programs by governmental agencies and various health groups and other interested organizations to disseminate information about the adverse health effects resulting from tobacco smoking. Moreover, and as a result of this recognition of the harmful effects, there have been many programs directed to attempts in reducing smoking incidence.

The present successes in achieving reduction in the incidence of smoking have been relatively poor with presently known techniques. The present state of the art involves both behavioral approaches and pharmacological approaches. Approximately 80% or more of the tobacco smokers who initially quit smoking after using some behavioral or pharmacological approach to singly reduce smoking incidence generally relapse and return to the habit of smoking at their former rate of smoking within about a one year's period of time.

One of the most successful approaches to date in reducing the incidence of smoking relies upon nicotine containing chewing gum which is designed to reduce smoking withdrawal symptoms. The reported success rate, while still relatively low is approximately twice that of the other methods which have heretofore been employed. The use of the nicotine gum suffers from several problems including not only the bad taste and destruction of dental appliances, but the gastrointestinal upset which results therefrom and which also reduces compliance. In addition, it has been found that the nicotine containing gum does not satisfy the craving that most smokers experience for the distinct sensations in the throat and chest elicited by nicotine in the smoke. Over the course of many years of tobacco smoking, these particular sensations have become an important part of and associated with the habit of smokers and give rise to tobacco smoke dependency in most of the tobacco smokers.

Transdermal administration of various drugs has been well known studies and includes the transdermal administration of cortisol, nitroglycerine and scopolamine. The latter two drugs are commercially available in the form of patches which are releasably applied to the skin for delivering controlled amounts of the drug. Transdermal drug administering patches of this type have been taught, for example, in U.S. Pat. No. 4,336,243 to Sanvordeker et al, U.S. Pat. No. 4,286,592 to Chandrasekaran, U.S. Pat. No. 3,731,683 to Zaffaroni and U.S. Pat. No. 3,797,494 to Zaffaroni.

The effects of using nicotine containing gum were described in detail in the British Medical Journal, Volume 286, dated Feb. 19, 1983. In addition, the nicotine absorption from tobacco leaves is well known. Farmworkers who hand harvest tobacco are at a serious risk of developing a self-limited illness often known as "green tobacco sicknes". Although mortality and long-term sequelae have not been associated with this syndrome, it is still responsible for discomfort and a substantial amount of lost work time. The use of protective clothing as a means to reduce body absorption of nicotine is set forth in the Archives of Environmental Health, March/April 1979, pages 111-113.

In addition to the above, the circulatory effects of nicotine aerosol inhalations have been studied as set forth in the Oct. 7, 1967 edition of the Lancet, pages 754-755. In this case, large doses of nicotine aerosols were applied to selected individuals in order to determine the effects on the individuals. Further, circadian blood nicotine concentrations have been studied as a result of cigarette smoking, as reported in Clinical Pharmacology and Therapeutics, December 1982 in an article by Neal L. Benowitz, M.D., pages 758-764.

A simulated smoking device which uses a source of a vaporizable nicotine is disclosed in U.S. Pat. No. 4,284,089 to Ray. While the cigarette itself is non-combustible, and delivers a vapor, it may not raise the nicotine level in the blood sufficiently to satisfy a smoker. Thus, it has not been shown to satisfy the desire for a certain nicotine level in the blood to which many smokers have become accustomed and, even moreso upon which many smokers have become dependent. In addition, the simulated smoking devices of the type taught in U.S. Pat. No. 4,284,089 also suffer from the bad taste of a substantial amount of nicotine introduced into the oral cavity. More importantly, this nicotine does not penetrate into the chest for stimulating and providing that sensation normally provided by nicotine and to which the smoker has become accustomed.

Heretofore, there has not been any attempt to transdermally administer nicotine to an individual in order to aid in the reduction of tobacco smoking. Moreover, there has not been any reported method of reducing the incidence of tobacco smoking by using a selected type of nicotine containing aerosol spray. In addition, there has not been any reported method or apparatus for reducing the incidence of tobacco smoking by using a combination of the aerosol spray and the transdermal administration of nicotine.

OBJECTS OF THE INVENTION

It is, therefore, one of the primary objects of the present invention to provide a method of aiding in the reduction of the incidence of tobacco smoking by transdermally allowing nicotine to migrate from a patch into a patient's bloodstream at a rate sufficient to correspond to the nicotine level in the blood which is achieved by the normal smoking patterns of the individual.

It is another object of the present invention to provide a method for allowing transdermal administration of the nicotine from a patch to the bloodstream at various time intervals which approximate the normal smoking pattern of an individual.

It is a further object of the present invention to provide a low concentration nicotine aerosol spray which has a selected droplet size and which also has a selected nicotine concentration to simulate the conditions and sensations normally obtained by the inhalation of tobacco smoke.

It is also an object of the present invention to provide a method of aiding in the reduction of incidence of tobacco smoking by administering nicotine containing aerosol spray with a selected size droplet and concentration in order to simulate the effects normally achieved by tobacco smoke.

It is another salient object of the present invention to provide a method of aiding in the reduction of incidence of tobacco smoking by using a combination of a transdermal administration of the nicotine as well as the nicotine containing aerosol spray.

It is still another object of the present invention to provide a device which enables the convenient and efficient dispensing of a nicotine containing aerosol spray.

With the above and other objects in view, our invention resides in the novel features of form, construction, arrangement and combination of steps and compositions as hereinafter described.

BRIEF SUMMARY OF THE DISCLOSURE

The invention relates in a broad aspect to a method of aiding in the reduction of incidence of tobacco smoking. In one embodiment, the method utilizes a transdermal application of nicotine and in another embodiment the method relies upon an oral application of a low concentration nicotine aerosol spray. In a further embodiment, the method relies upon a combination of the transdermally applied nicotine as well as the low concentration nicotine aerosol spray.

It has been found that one of the principal problems in reducing the incidence of smoking and promoting cessation of tobacco smoking is the fact that the smoker, after a period of time, has become accustomed to and acquired a certain dependency to a certain nicotine level in the bloodstream. It is believed that this dependence upon nicotine level may be a mild form of addiction. Nevertheless, it has been found that with many smokers, it is necessary to provide an alternative source of the nicotine to maintain at least a portion of this nicotine level in the smokers bloodstream if the incidence of smoking is to be reduced. By providing a substitute source of nicotine, it is possible to thereby eliminate the harmful effects of smoking.

It has also been found that the average smoker, after a period of time, has become accustomed to and perhaps depends upon a certain mild irritation or tingling sensation in the throat and respiratory tract which results from the nicotine contained in the tobacco smoke. In many cases, it has been found to be desirable to replace this sensation of mild irritation in the respiratory tract with something other than a high concentration of the nicotine normally found in tobacco smoke.

In the transdermal application of nicotine, a selected amount of nicotine is applied to a dermally applicable patch and this patch is then placed on the skin of the person in whom smoking reduction is desired. This allows the nicotine in the patch to transdermally migrate into the persons bloodstream at a rate sufficient to correspond to the nicotine level in the blood normally achieved by that users smoking patterns.

In one embodiment, nicotine levels in the bloodstream can be measured at spaced apart time intervals to thereby control the amount of nicotine applied to the patch in order to achieve nicotine levels in the bloodstream approximating those at the various spaced apart time measurements. Thus, by applying nicotine in a level approximating that obtained by the smoker's normal smoking patterns, there is a reduced need for the smoker to obtain the nicotine as a result of tobacco smoking and with the reduced attendant harmful side effects of smoking.

The low concentration low dose nicotine aerosol spray is also used for reducing the incidence of smoking, as aforesaid, by simulating the effects in the respiratory tract normally obtained from tobacco smoke. The aerosol spray preferably has droplets within a size range of about between about 1 micron to about 10 microns in diameter. Size is selected to stimulate either the upper respiratory tract or the lower respiratory tract or both. Further, the spray and each inhalation thereof contains nicotine in an amount of about 0.005 mg to about 0.03 mg per inhalation.

In a more preferred embodiment, the spray has droplets of a size range of about 1 micron to about 5 microns for stimulating the lower respiratory tract and droplets within a size range of about 5 microns to about 10 microns for stimulating the upper respiratory tract. Even more preferably, the nicotine spray contains from about 0.008 mg per inhalation to about 0.015 mg per inhalation.

This invention possesses many other advantages and has other purposes which will be made more clearly apparent from a consideration of the forms in which it may be embodied. They will now be described in detail for purposes of illustrating the general principles of the invention, but it is to be understood that such detailed descriptions are not to be taken in a limiting sense.

BRIEF DESCRIPTION OF THE DRAWINGS

Figure 1:
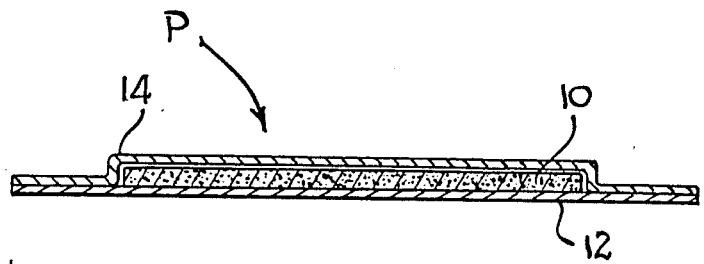
Figure 2:
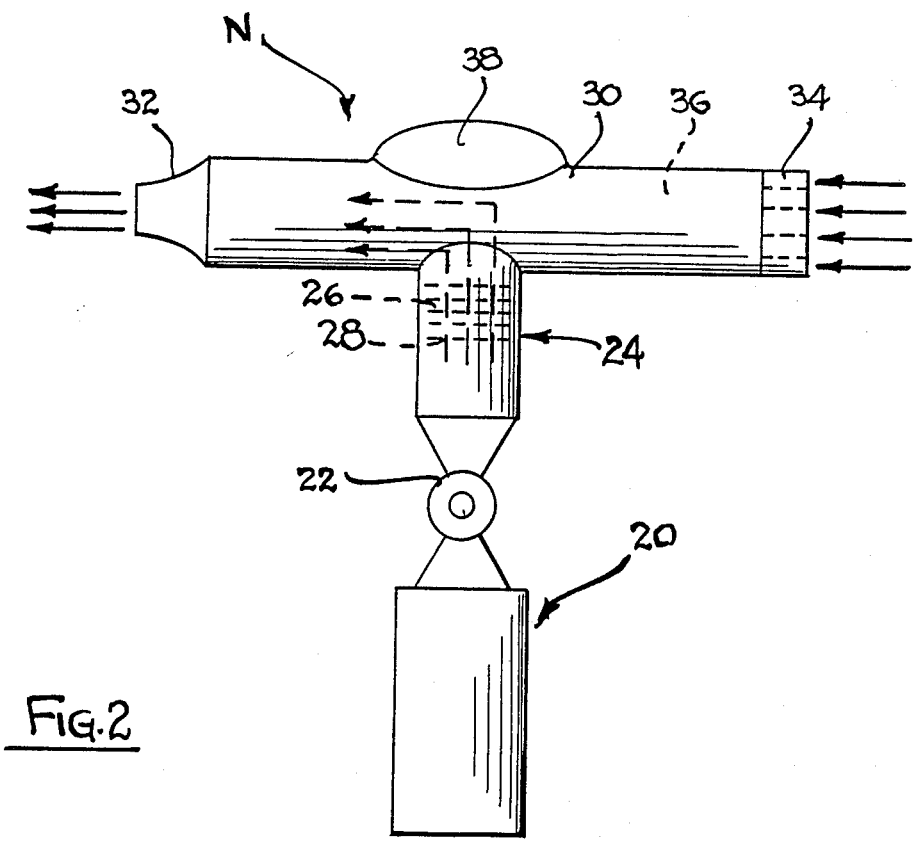
Figure 3:
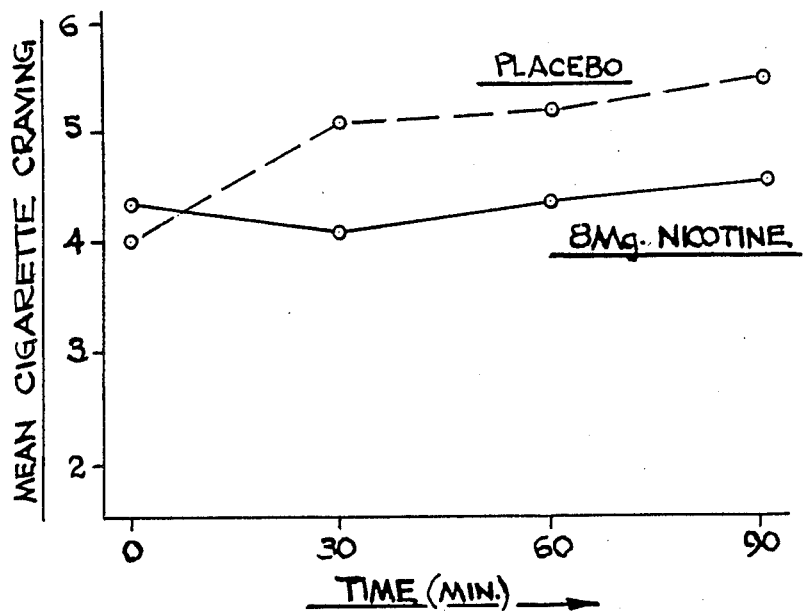
Figure 4:
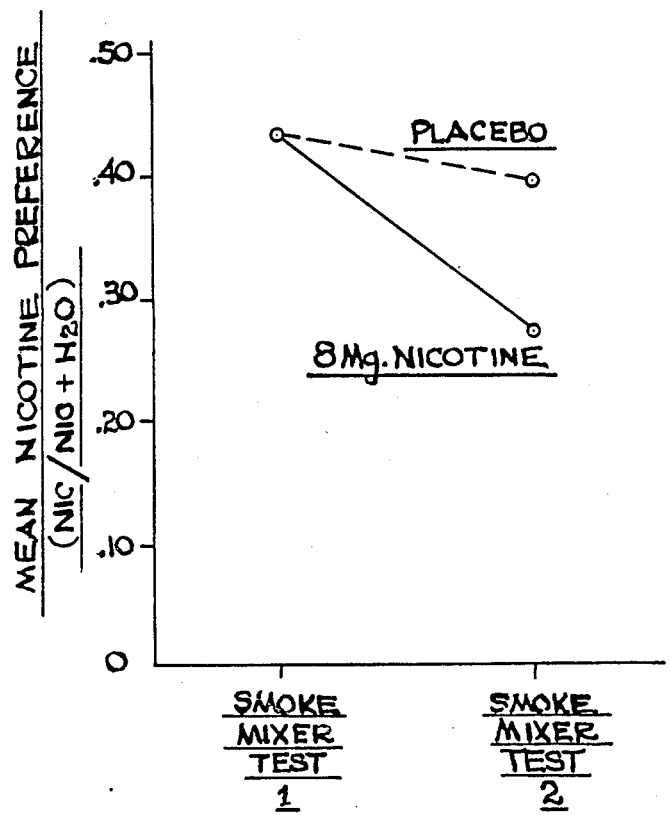
Figure 5A:
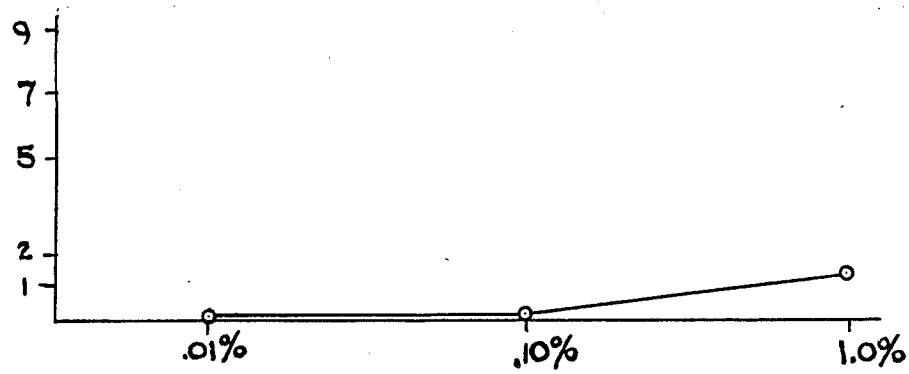
Figure 5B:
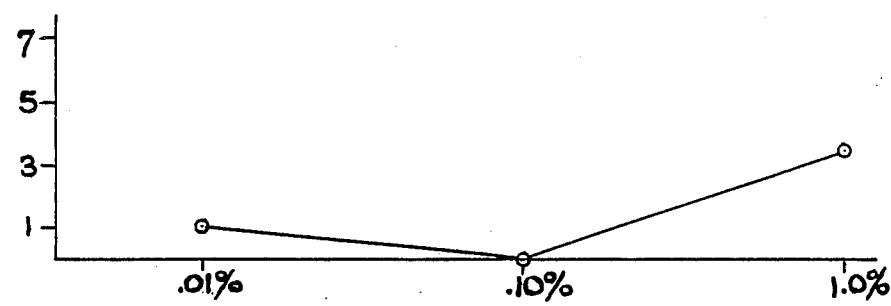
Figure 5C:
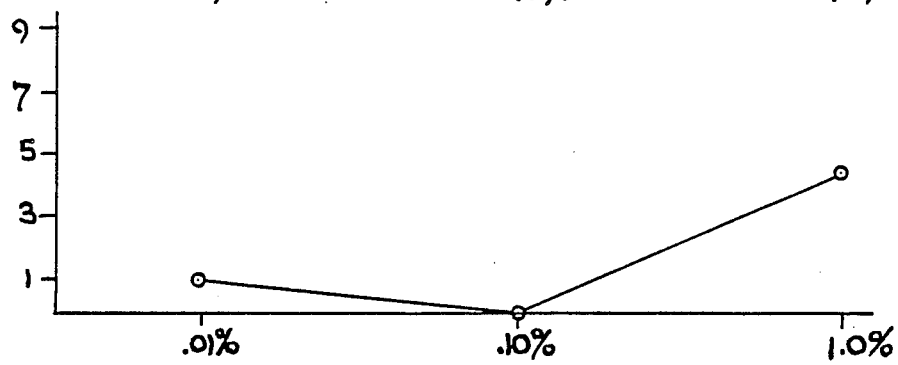
Figure 5D:
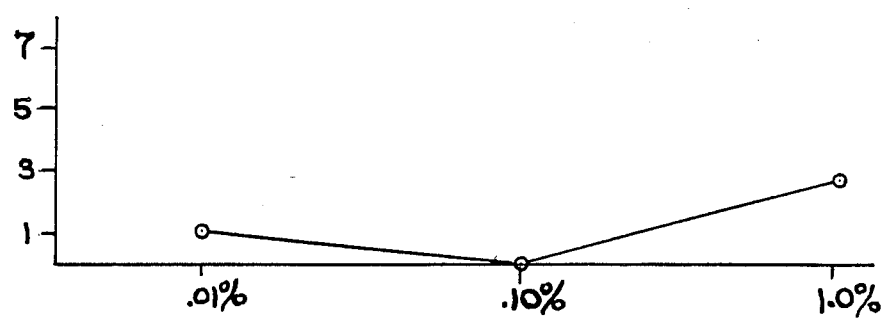
Figure 5E:
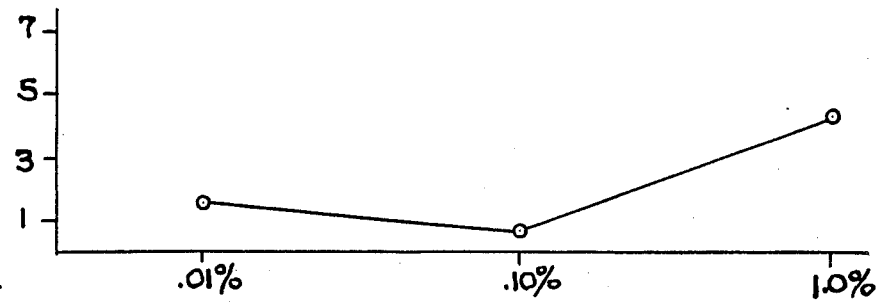

Having thus described the invention in general terms, reference will now be made to the accompanying drawings in which:

FIG. 1 is a somewhat schematic vertical sectional view of a patch for the transdermal administration of nicotine;

FIG. 2 is a schematic side elevational view of a nebulizer which may be used for the oral administration of a low dose nicotine aerosol spray; and FIG. 3 is a graph showing the effects of transdermal nicotine on mean cigarette craving as a function of time;

FIG. 4 is a graph showing mean nicotine preference with transdermal nicotine and a placebo; and FIG. 5 is a composite of FIGS. 5A through 5E showing various effects on users as a function of the percentage of nicotine contained in an aerosol spray.

DETAILED DESCRIPTION OF PREFERRED EMBODIMENTS

With reference to the accompanying drawings, FIG. 1 illustrates a dermally applied nicotine applicator, in the form of a patch P, which is adapted for application to a suitable portion of a smoker's body, as for example, on a forearm or chest of the individual, or the like.

The patch illustrated in FIG. 1 comprises a pad 10 which comprises a somewhat absorbent material capable of functioning as a reservoir for nicotine and which is secured to a lower adhesive layer 12. This adhesive layer may be provided with a releasable backing (not shown). In addition, the pad 10 is covered on its upper surface by means of an outer enclosing layer 14. The adhesive layer 12 is sufficiently porous so that nicotine contained within the pad 10 may be transdermally applied to the user of the patch. In addition, and for this purpose, small apertures could be formed within the adhesive layer 12 if desired.

The pad 10 may be formed of a cotton material or similar cloth-like material which is capable of retaining, but yet dispensing a liquid carrier which holds the nicotine. The pad may also be formed of a silicone polymer matrix comprised of a cross-linked silicon rubber and having micro-sealed compartments which are effectively formed by the in-situ cross-linking of the silicon rubber. Other forms of dermally applicable patches which can be used in connection with the present invention are illustrated for example, in U.S. Pat. No. 3,797,494 to Zaffaroni, U.S. Pat. No. 3,731,683 to Zaffaroni, and U.S. Pat. No. 4,336,243 to Sanvordeker et al.

The pad preferably has a size of about two centimeters by two centimeters at a minimum. Preferably, the patch has a surface area of about five centimeters by five centimeters with a thickness of about two to three millimeters. There is no effective outer limit on the size of the patch except for convenience. The nicotine is present in an amount so that it may deliver a few miligrams per hour, as hereinafter described in more detail. Thus, for a twenty-four hour delivery period, the patch should have a size and thickness to retain a minimum of fifty miligrams of nicotine.

The patch described herein can be placed on any convenient area of the users skin, such as, the underside of the forearm of the users body or on the chest of an individual. In this way, when the patch is applied to the users body it will release a continuous supply of nicotine to the smoker.

The nicotine is preferably dissolved in an inert liquid vehicle, such as, for example, K-Y jelly or any other liquid carrier which does not react with the body or with the nicotine and which readily permits transdermal migration of the nicotine. One of the primary liquid carriers which may be used is water. However, various low molecular weight alcohols, such as ethanol, etc. could be used. In addition, glycerol, propylene glycol, petrolatum, etc are effective carriers for the nicotine.

The nicotine is added to the liquid carrier in an amount of about 15% by weight to about 50% by weight, particularly when water is the liquid carrier. More preferably, the nicotine is added to the liquid carrier in an amount of about 25% to about 35%. Nicotine present in an amount of about 30% by weight has been found to be highly effective. The amount of nicotine to be added to the carrier is a function primarily of the desired rate of delivery, as hereinafter described, and is, in turn, a function of e.g. patch size, pH of the carrier, etc.

The carrier preferably has a pH of no higher than about 8 or 9, although it can be made less basic or more acidic, as hereinafter described, in order to control nicotine penetration rates. Nicotine is well known to penetrate the intact skin, particularly at a pH of about 7 or greater. As indicated previously, tobacco farmers sometimes suffer nicotine poisioning when handling tobacco with bare hands.

It is also possible to add to the liquid carrier an agent to increase the permability of the skin, such as dimethyl sulfoxide (DMSO) or equivalent agent. The dimethyl sulfoxide is a topical agent which facilitates penetration of the nicotine through the skin. It is possible to use the dimethyl sulfoxide in an amount of about 100% in place of the liquid carrier, although it could have some adverse side effects to the user, such as rendering an unpleasant taste in the user's mouth. Nevertheless, dimethyl sulfoxide or other equivalent agent could be added in an amount of about 40% to about 70%. Other similar acting agents which can be used include, e.g., sodium lauryl sulfate, 1-dodecylhexahydro-2H-azepin-2-one (Azone) and a mixture of propylene glycol and oleic acid.

A nicotine antagonist may be incorporated into the patch, as for example, hexamethonium. The hexamethonium or other equivalent anti-inflammatory agent could be included within the patch to act as a peripheral blocking agent. In this way, it is possible to block peripheral side effects of the nicotine, as for example, local skin irritation. It is also possible to reduce cardiovascular side effects without significantly blocking the therapeutic effect of nicotine which results from reducing the dependency on tobacco smoking. In addition to hexamethonium, it has been found that pentolinium can also be used as a nicotine antagonist. Hexamethonium and pentolinium are preferred inasmuch as they do not enter the brain in significant quantities but have been found to be highly effective in blocking the peripheral actions of the nicotine. The nicotine antagonist should be included in a minor amount of about 10 mg. to about 20 mg. by weight in the liquid carrier.

Various modifications to the patch can be made in order to vary the dose and rate of nicotine absorption into the users bloodstream. It is important to provide a patch such that nicotine administration can approximate the level of nicotine in the bloodstream of the user which is normally achieved through tobacco smoking.

One of the techniques which can be used in order to determine nicotine levels in the bloodstream as a result of smoking is to measure the actual nicotine percentage contained in the bloodstream immediately after the smoking of a cigarette. These measurments can be made several times over a typical day of the smoker, including prime points immediately before and after the smoking of the cigarettes. Inasmuch as some smokers typically achieve large plasma nicotine peaks immediately after smoking and others achieve large plasma nicotine peaks gradually, the transdermal patch and the method of use thereof can be conveniently and easily tailored to the particular user.

There are several techniques which can be used to control the rate of absorption of nicotine by the body. The stratum corneum is one of the largest barriers to diffusion of most substances into the body, including that of the nicotine and the inert carrier. Thus, abrading the skin slightly to remove the outer epidermis layer facilitates the absorption of nicotine and thereby produces larger peak nicotine levels. Another technique for increasing the absorption of nicotine is by the addition of a skin permeability increasing compound to the liquid carrier, such as the dimethylsulfoxide compound. Other known compounds can also be used to increase the rate of absorption by increasing skin permeabilty.

In addition to the foregoing, it has been found that the shape of the patch also has some effect on the rate of the diffusion of nicotine from the patch into the bloodstream. Particularly, the depth and the surface area of the patch are a function of the rate of nicotine absorption by the body. Using a larger surface area increases the rate of the absorption and a thinner pad also increases the rate of absorption. Thus, a thin wide patch with large surface area would facilitate absorption and a relatively thick patch with small surface area would diminish the rate of absorption.

It is also possible to include a rate controlling membrane on the patch which would be permeable to nicotine. Such a membrane would retard the absorption of the nicotine and provide lower sustained plasma levels of nicotine for the smoker. Some of the rate controlling membranes which can be employed are microporous films as for example, those membranes taught in U.S. Pat. No. 4,060,084.

The nicotine is generally a basic substance and renders a pH of about 8 or 9 to the liquid carrier and the ingredients carried thereby. Lowering of the pH somewhat tends to eliminate the adverse inflamatory effects of nicotine. However, as the pH is reduced, the rate of administration of the nicotine to the blood stream is correspondingly reduced. Thus, it is preferable not to reduce the pH below 7.0. It is, however, effective to use the pH in controlling the rate of diffusion of the nicotine into the body.

The use of the transdermally applied patch has been found to be effective in reducing the incidence of smoking in absence of any behavioral or pharmacological treatment for facilitating smoking cessation or the incidence of smoking. The technique of nicotine substitution allows the user to have a sustained blood level of nicotine to which the user has become so accustomed or dependent, without the serious adverse side effects which result from tobacco smoking. Moreover, the transdermal application of nicotine avoids the significant disadvantages over the buccal application achieved with nicotine containing chewing gum.

The nicotine containing chewing gum has aversive side effects resulting from the direct contact of nicotine on the lining of the oral cavity which can result in sores and sensitivity. Adverse side effects such as irritation to the esophagus and stomach can also result. Thus, the nicotine containing chewing gum has the serious side effects of bad taste, heartburn, nausea, etc. and all of these are eliminated by the transdermal application of nicotine. Moreover, inasmuch as the rate of application can be controlled, the nicotine chewing gum and other nicotine sources which previously required applications throughout a day, can now be eliminated.

The transdermal patch is constructed with proper dimensions so that at least eight milligrams of nicotine is contained in the patch in absence of any penetration enhancer, such as the DMSO. Without a penetration enhancer, there is no absolute maximum amount, although twenty milligrams would be a reasonable maximum amount of nicotine. With the penetration enhancer incorporated into the carrier, the amount of nicotine can be as low as one to two milligrams and as much as about four to five milligrams.

These nicotine amounts are desirable so that nicotine can be applied to the persons bloodstream in desired amounts. At the start of a smoking reduction program it is desired to have about ten nanograms of nicotine per milliliter of blood in the persons bloodstream. This, in effect, means that there is about at least fifty micrograms of nicotine in the persons bloodstream at the start of a smoking reduction program. In some cases, for heavy smokers who are accustomed to a greater amount of nicotine, the blood level could be as much as two hundred fifty micrograms although generally the nicotine level in the blood should not exceed about one hundred micrograms. After a period of time, the amount of nicotine which is transdermally applied can be reduced and this enables the smoker to easily and comfortably reduce the dependency on nicotine and hence on tobacco smoking.

The present invention also provides a method of using a nicotine containing aerosol spray which may be dispensed from a nebulizer N, as shown in FIG. 2. The nebulizer generally comprises a container such as a bottle 20 containing a solution of nicotine dissolved in a liquid carrier. Located at the upper end of the container 20 is a valve 22, which may be in the form of a pushbutton valve or one with a rotatable valve core capable of being manually manipulated by a user, such that the nicotine containing carrier can be dispensed from the container upon opening of the valve 22. Located above the valve is a housing 24 having a plurality of internally located baffles 26. Each of these baffles 26 would have apertures 28 contained therein which control the size of the nicotine vehicle droplets. The upper end of the housing 24 is connected to and in fluid communication with an inhalation tube 30 which has a reduced end 32 for introduction into a user's mouth. The opposite end of the tube 30 may have a screen 34 over the open end thereof in order to strain and remove any foreign particles in an entering air stream.

The tube 30 has an internal chamber 36 which is designed to receive a charge of the aerosol spray. The tube 30 may also be provided with an enlarged hump 38 as shown in order to increase the overall size thereof and to insure that the content of the nicotine containing liquid gaseous carrier within the tube is sufficient to constitute one full inhalation with a desired amount of nicotine.

The bottle 20 is preferably a pressurized bottle containing an inert gas under pressure. Various inert gases, such as Freon or the like, which are normally found in containers of this type, may be employed.

The screen 34 may take the form of a resistive member which somewhat restricts the flow of air therethrough. In this way, the screen can act as a cigarette filter which creates a draw resistance much in the same manner as one experiences when drawing air through a cigarette. For that matter, a conventional cigarette filter could be fitted upon the right-hand end of the tube 30.

The nicotine is mixed with the liquid carrier in an amount of about 0.5% to about 3% by weight. However, preferably, the nicotine is contained in the liquid carrier in an amount of about 1% by weight. In any event, it is desirable to include the nicotine in the carrier in an amount so that there is about 0.01 milligram per inhalation.

Some of the liquid carriers which are used in the transdermal patch can be used in the case of the aerosol spray. Generally, those liquid carriers which are employed in various inhalers, as for example, inhalers in bronchial dilators may be used.

It is also possible to add one or more surfactants to the liquid carrier in order to break up the nicotine entrained droplets into smaller sizes. Lecithin is one excellent surfactant which can be used inasmuch as it is highly compatable with body tissue. Other surfactants which may be considered for use include sorbitan trioleate, cetylpyridinum, etc. If a surfactant is used, it is preferably added in an amount of about 0.5% to about 1.0% by weight.

When the user desires to obtain one inhalation equivalent to that from a puff from a cigarette, the user merely opens the valve 22 allowing the inert gas to move the nicotine containing liquid carrier through the baffles 26 and into the internal chamber 36 of the tube 30. The apertures in the baffles control the size of the droplets which are formed. As indicated, the charge of liquid droplets, which is actually in the form of a fine mist, in the chamber 36 is sufficient to effectively constitute one complete inhalation containing the desired amount of nicotine. At this point, the user merely sucks on the reduced end 32 causing a stream of air to pass through the filter or screen 34 and the tube 30 thereby drawing the charge contained in the chamber 36 into the users oral cavity which is subsequently inhaled, as with a puff of cigarette smoke.

The oral application of nicotine in an aerosol spray is highly effective inasmuch as it contains a relatively small percentage of nicotine and thereby avoids many of the harmful side effects of nicotine contained in large quantities in a nicotine containing chewing gum or the substantial quantities of nicotine contained in normal tobacco smoke. The low concentration nicotine aerosol spray provides the smoker with those sensations which were normally produced by smoking but with a substantially lesser percentage of nicotine.

In normal tobacco smoke, approximately 0.1 mg of nicotine is obtained in each puff of a medium strength cigarette. This quantity of nicotine is known to provide the smoking related tracheal sensations. However, by using a low concentration nicotine spray of approximately 0.008 mg to about 0.03 mg per inhalation, and preferably about 0.1 mg, and by controlling these droplet sizes it is possible to obtain the same effect. This is due to the fact that the size of the droplets determines the region of the respiratory tract to which the nicotine would penetrate. For example, by using droplets within a range from about 1 micron to about 5 microns the nicotine containing droplets will penetrate to the lower respiratory regions for stimulation of those regions. Larger droplets, as for example, 5 microns to about 10 microns would not penetrate very deeply in the respiratory tract and thus would stimulate the higher respiratory tract regions. Thus, by controlling the droplet size, it is possible to stimulate that portion of the respiratory tract from which the smoker receives the greatest sensation. In addition, inasmuch as the nicotine is allowed to penetrate to the desired regions, in controlled amounts, it is not necessary to employ the large quantities of nicotine normally contained in nicotine containing chewing gum and in normal tobacco smoke.

The amount of nicotine contained in the aerosol can range, as aforesaid. However, it is desired to maintain a relatively low concentration of nicotine in order to reduce the excessive harshness to the respiratory tract. It is also possible to increase or decrease the size of the droplets in combination with the concentration of the nicotine in order to simulate the effects normally obtained by the smoker from tobacco smoking.

It has been found with some individuals that the mere application of the nicotine containing spray is sufficient to reduce the strong desire for cigarette smoking. Thus, and with many patients, it is possible to reduce the incidence of smoking with either the transdermal patch or the oral application of a low concentration aerosol spray.

In many cases, individually the habitual smoker requires both the systemic levels of nicotine in the bloodstream as well as the sensations normally provided by nicotine in the respiratory tract. In this case, the nicotine containing aerosol spray and the transdermal patch operate in a complimentary manner with the transdermal patch allowing nicotine concentration in the bloodstream to which the smoker is accustomed and also allows the sensations normally provided in nicotine containing tobacco smoke. Further, the transdermal patch allows the nicotine concentration in the spray to be reduced to a desired level and which may vary from patient to patient.

The disassociation of the local tracheal stimulation produced by nicotine from its sysemic physiological effects also is believed to allow for an effective extinction training procedure. Thus, the prior conditioning of the smoker in which smoke elicited throat stimuli were paired with the desired pharmacologic effects of nicotine in each puff can be reversed. For example, the nicotine aerosol spray could be presented at different times of the day from the transdermal patch. Under normal conditioning theory this is believed to hasten the extinction of the tracheal desire. A presentation of tracheal stimulation without an effective dose of nicotine reduces the association with the nicotine's desired effects. Further, presentation of nicotine's effects via the transdermal patch and without the tracheal stimulation also degrades the previously learned association between the local respiratory effects and the pharmacologic effects of nicotine.

EXAMPLES

This invention is further illustrated by but not limited to the following examples:

EXAMPLE I

One subject who was an adult male who did not smoke or consume any tobacco products, was tested using a transdermal patch as described herein.

The tested subject abstained from all caffeine and alcohol intake for a period of at least twelve hours prior to testing. After baseline readings of pulse and blood pressure (15 minutes and immediately prior to nicotine administration) nine milligrams of nicotine was applied in a 30% aqueous solution to the underside of the left forearm of the subject. This was covered by a thin layer of polyethylene to prevent evaporation and taped in place.

Systemic nicotine levels were non-invasively monitored in the saliva of the subject and which was collected by having the subject expectorate into a vial. The saliva samples were collected at 15 minutes before the application of the nicotine, at the time of the application of the nicotine and 15 minutes, 30 minutes, 60 minutes, 90 minutes, 120 minutes, 180 minutes, 220 minutes, 240 minutes, 360 minutes, 480 minutes and 720 minutes respectively thereafter. Due to the fact that subject was not a smoker, the possibility of direct contamination of saliva by nicotine in smoke was ruled out.

Saliva pH was measured with a Corning Model No. 12 pH meter to 0.1 units. The samples were then evaluated for biochemical analysis. The results were highly accurate due to the fact that the measurements were made with a high pressure liquid chromatography technique. The results revealed that the saliva nicotine levels were approximately 75 milligrams per milliliter within 2 hours after the topical administration of the 9 milligrams of nicotine.

EXAMPLE II

The same subject of Example I was used and the physiological measurements were taken as an index of the nicotine's effects on this subject. The radial pulse was counted for two successive minutes at each time point and the values were averaged. Systolic and diastolic blood pressure were also measured. It was determined that within 30 minutes the salivary nicotine content rose to a level of 50 milligrams per milliliter and reached a peak at 90 minutes of 85 milligrams per milliliter. These levels were determined to be comparable to those produced by cigarette smoking.

The relative concentrations of nicotine in saliva and the blood is pH dependent. In the test results, the salivary pH remained approximately 7 over the course of the entire study and the expected ratio of saliva to blood nicotine concentrations was approximately 2 to 1. The increase in salivary nicotine was maintained over 2 hours after which it gradually declined and by 12 hours did not differ from any baseline level.

Physiological measures were plotted for comparison. The heart rate increased substantially during the first 30 minutes and reached a level commonly achieved by smokers after consuming the first cigarette of a day. Systolic and diastolic blood pressures also increased generally and the physiological indices paralleled the nicotine levels observed in saliva ($r=0.63$, 0.88, 0.57; $p$ less than 0.05, for heart rate, systolic and diastolic blood pressure, respectively). The heart rate and systolic blood pressure remained elevated for a short period after nicotine levels had declined to baseline levels, which was generally believed to be due to the greater sensitivity of these responses to low concentrations of nicotine or hormonal effects triggered by the nicotine. As used herein "r" is a correlation coefficient which effectively describes the association between nicotine levels in saliva and heart rate and systolic and distolic pressure. The term "p" is the probability that the observed relationship would be due to chance alone. A p of less than 0.05 would mean that the probability of observing the association due to random chance alone is likely.

EXAMPLE III

A group of subjects are tested using transdermal patches as described herein. The subjects tested, are generally cigarette smokers containing some individuals who smoke a few cigarettes a day to some individuals who smoke as as many as forty or more cigarettes per day.

All subjects tested abstain from all caffeine and alcohol for a period of at least twelve hours prior to testing. After baseline readings of pulse and blood pressure (15 minutes and immediately prior to nicotine administration) nine milligrams of nicotine is applied in a 30% aqueous solution to the underside of the left forearm of each of the subjects. This was covered by a thin layer of polyethylene to prevent evaporation and taped in place.

Systemic nicotine levels are non-invasively monitored in the saliva of the subjects and are collected by having the subjects expectorate into individual vials. The saliva samples are collected 15 minutes before the application of the nicotine, at the time of the application of the nicotine and 15 minutes, 30 minutes, 60 minutes, 90 minutes, 120 minutes, 180 minutes, 220 minutes, 240 minutes, 360 minutes, 480 minutes and 720 minutes respectively thereafter.

Saliva pH for each subject is measured with a Corning Model No. 12 pH meter to 0.1 units. The samples are then evaluated for biochemical analysis. The results reveal that the saliva nicotine levels are approximately 75 milligrams per milliliter within 2 hours after the topical administration of the 9 milligrams of nicotine.

EXAMPLE IV

The same subjects of Example III are used and the physiological measurements are taken as an index of the nicotine's effects on these subjects. The radial pulse of each subject is counted for two successive minutes at each time point and the values are averaged. Systolic and diastolic blood pressure is also measured. It is thus determined that within 30 minutes the salivary nicotine content rose to a level of 50 milligrams per milliliter and reaches a peak at 90 minutes of 85 milligrams per milliliter. These levels are determined to be comparable to those produced by cigarette smoking.

The relative concentrations of nicotine in saliva and the blood is pH dependent. In the test results, the salivary pH remains approximately 7 over the course of the entire study and the expected ratio of saliva to blood nicotine concentrations is approximately 2 to 1. The increase in salivary nicotine is maintained over 2 hours after which it gradualy declines and by 12 hours does not differ from any baseline level.

Physiological measures are plotted for comparison. The heart rates of the subjects increases substantially during the first 30 minutes and reaches a level commonly achieved by smokers after consuming the first cigarette of a day. Systolic and diastolic blood pressures also increase generally and the physiological indices parallels the nicotine levels observed in saliva ($r=0.63$, 0.88, 0.57; $p$ less than 0.05, for heart rate, systolic and diastolic blood pressure, respectively). The average heart rate and systolic blood pressure remain elevated for a short period after nicotine levels decline to baseline levels.

EXAMPLE V

The effects of transdermal nicotine administration on ten cigarette smokers were studied. The subjects smoked an average of 29 (s.d.$=10.8$) cigarettes per day with a nicotine delivery (FTC method) of 0.9 mg (s.d.$=0.20$). These subjects were chosen from a group who showed evidence of nicotine dependence in a preliminary screening session by comparing nicotine preference after 12 hours smoking abstinence with that immediately after smoking (10 puffs from a Marlboro Lights 100's cigarette delivering 0.7 mg nicotine). Nicotine preference was determined using a smoke mixing device (described below) with which subjects controlled the nicotine concentration of each puff.

Subjects were classified as nicotine dependent if nicotine preference was higher after overnight abstinence than after smoking. Fourteen of twenty three subjects screened (61%) were classified as nicotine dependent, and ten of these were chosen at random to complete the study.

High and low nicotine cigarettes were used in a smoking-mixing device to measure subjects' nicotine preference. In order to insure that cigarettes differed only in nicotine delivery, commercial Marlboro Lights 100's cigarettes were used and added either distilled water or a small amount of nicotine base to the filter. Twenty microliters of water or 30% aqueous nicotine (6 mg) were injected approximately 1 cm axially into the cigarette filters. When smoked, the nicotine delivery of the nicotine-injected cigarettes was enhanced. To quantify the nicotine delivery, artifical smoking procedures were used that approximated FTC criteria (35 cc puffs taken 1/min to a cigarette length of 3 mm in excess of filter and overwrap) and analyzed the residue trapped in Cambridge filter pads. The nicotine delivery of the low nicotine control cigarettes was found to agree with published values for that brand ($0.73 \pm 0.03$ mg v. $0.75 \pm 0.02$ mg), whereas nicotine-injected cigarettes delivered $1.5 \pm 0.1$ mg nicotine. Tar delivery was unaffected by the nicotine injection technique.

To control the nicotine delivery of each puff, the subjects used a smoke mixer which blended smoke in graded amounts from the high and low nicotine cigarettes just described. By turning a knob the subjects could select any intermediate nicotine delivery desired. A dial reading ranging from 3.0 to 7.0 in 0.1-unit steps indicated the position of the knob on any given puff. However, the device was modified so that a portion of smoke (15%) delivered through the high and low nicotine sides was diverted and trapped in the Cambridge filter pads. By weighing the residue the total particulate matter drawn into the smoker's mouth as well as the proportion of smoke selected from the high and low nicotine cigarettes was estimated.

Nicotine or a placebo was topically applied under a 5 cm $\times$ 5 cm polyethylene patch to the various subjects. Nicotine base was administered in a 30% aqueous solution and the placebo consisted of a solution of food coloring in water that mimicked the color and was visually identical to the nicotine solutions. The volume of solution (26 microliters) was equal to that of the 8 mg nicotine dose. An opaque polyethylene patch covered the area to prevent subjects from observing any changes in skin color (e.g. redness).

Because the ratio of nicotine concentration in saliva to that in blood is pH dependent, saliva pH was measured to the nearest 0.1 unit using a Corning Model 12 pH meter.

Expired air CO levels were measured with an electrochemical analyzer (Ecolyzer Model A) before and after each nicotine preference test, to estimate smoke inhalation. Samples were collected after 20 second of breath holding and discarding the first 500 cc of expirate to eliminate dead space air from the sample.

The subjects were tested on three consecutive afternoons, without having abstained from tobacco. The subjects were informed that either nicotine or placebo would be administered transdermally.

On all days the testing began with a nicotine preference test in which subjects were instructed to first take a puff from the middle, low and high nicotine settings of the smoke mixer. Then they were allowed to smoke freely for 10 min., adjusting the nicotine delivery of each puff to the level desired. The sides of the mixer in which the high and low nicotine cigarettes were placed were counterbalanced across subjects. The subjects recorded the mixer dial reading to the nearest 0.1 unit and rated the strength, harshness and desirability of each puff.

Following the preference test subjects received, double-blind, either 0, 4 or 8 mg nicotine in a transdermal patch taped to the volar surface of the nondominant forearm. The skin was cleansed with 70% isopropyl alcohol before application of the patch. The 4 mg dose was always administered on the first day as a safety precaution and was not included in any data analyses. No adverse reactions were noted in any subject for this dose or for the subsequent 8 mg dose. The 0 and 8 mg doses were presented on days 2 and 3 in counterbalanced order.

After applying the transdermal patch, subjects were not allowed to smoke for 90 min. Every 30 min the subjects filled out questionaires to assess smoking withdrawal symptoms. Heart rate, an index of nicotine effects, was also measured at these times by counting the radial pulse for 30 sec.

To monitor the absorption of transdermal nicotine, saliva samples were collected every 30 min for subsequent nicotine analysis. Saliva flow was stimulated by having subjects hold a sugar cube in the mouth and expectorate into a vial. Saliva pH was measured to estimate blood nicotine levels from the expected ratio of nicotine in the free base form (which passes readily between saliva and blood) to that in the positively charged form (which does not readily pass between saliva and blood). Before stimulating saliva flow, subjects rinsed their mouths 3 times with water in order to minimize any contamination of saliva by nicotine previously ingested in cigarette smoke.

Ninety minutes after the patch was applied, a second nicotine preference test was administered. Transdermal patches were removed at the end of the session, and subjects were asked to indicate whether they believed they had received nicotine or placebo.

Saliva samples collected 30 min after application of the patch were analyzed for nicotine. The accuracy of the high pressure liquid chromatography technique employed was $\pm 10\%$. The saliva nicotine concentrations were transformed to yield estimated blood levels, using a correction factor based on the relative pH of saliva and blood.

The pH of plasma was assumed to be 7.4 and the pKa of nicotine at 37 degrees C. was taken to be 7.75.

The withdrawal questionaire data were scored according to a previous factor analysis validation study, which resulted in the following scales: Craving, Arousal, Appetite, Psychological Symptoms, and Physical Symptoms.

Three indices of nicotine preference during the smoking periods were calculated and included (1) the mean per portion of particulates obtained from the high side of the smoking mixer and which was determined by weighing residue traped in a filter pad in the mixer, (2) the mean preference for the nicotine cigarette, as calculated from settings recorded for each puff by each subject, and (3) the change in puff desirability rating with increasing nicotine content. The craving was measured by requesting each of the subjects to fill out repeated questionaires. The craving increased significantly over time and there was a significant (nicotine X time) interaction. The craving increased differentially with respect to placebo users. The craving as a function of time is plotted in FIG. 3 showing the eight milligram nicotine content versus the placebo.

In view of high peak plasma nicotine levels produced by smoking, the effects of transdermal nicotine on nicotine preference were assessed during the first two puffs of the smoke mixer tests. Measurements were made with the first two puffs to insure that subsequent puffs did not over-shadow the effects of the transdermal nicotine. Nicotine preference was lower in the eight milligram nicotine condition 90 minutes after the transdermal patch was applied. The results of this test are shown in FIG. 4. Two smoke mixers were used with the subjects and are identified as smoke mixer test No. 1 and smoke mixer test No. 2 in FIG. 4. The tests revealed that with a placebo, nicotine preference did drop slightly, although with the transdermal patch containing eight milligrams of nicotine, the nicotine preference dropped markedly.

EXAMPLE VI

In order to examine the interrelationship between measures of smoking as determined in Example V, a principal components analysis was made on the following eight dependent variables: (1) cigarette craving reported immediately before the smoke mixer test; (2) increase in expired air CO after smoking; (3) total smoke particulates taken from both cigarettes in the mixter; (4) number of puffs taken from the smoke mixer; (5) proportion of smoke obtained from the high nicotine cigarette (measured by trapped particulates); (6) the slope of the regression line relating puff desirability to nicotine content; (7) nicotine preference during the first two puffs; and (8) nicotine preference during the last two puffs. The value of each variable was summed across the four smoke mixer test periods (mixer test 1 and 2 on the 8 mg nicotine and placebos) to provide a representative index. Only factors with Eigenvalues greater than 1 were retained. The significance of each Eigenvalue was evaluated with the Chi-square test.

Two substantial factors emerged ($p<0.01$ for factor (1) and $p<0.02$ for factor (2) which together accounted for 84% of the total variance). Varimax rotation yielded a simplified factor structure (see the following Table 1). The first factor (smoke) encompassed variables 1-4, which comprised all of the cumulative measures of smoke intake, including craving. The second factor (Nicotine) consisted of all of the variables postulated to be specific measures of nicotine preference (variables 5-8). The residual correlation matrix after extropolation of these two factors was not significant ($p>0.5$).

TABLE I

Principal Components Analysis of Smoking Variables

Rotated Factor Loadings

| Variable | Factor 1 (smoke) Eigenvalue = 3.76 | Factor 2 (Nicotine) Eigenvalue = 2.97 |
|---|---|---|
| (1) Craving | .938 | −.096 |
| (2) CO increase | .906 | −.305 |
| (3) Total smoke intake | .900 | −.254 |
| (4) Number of puffs | .840 | −.288 |
| (5) Proportion high-nicotine smoke | −.303 | .892 |
| (6) Nicotine desirability | .069 | .874 |
| (7) Nicotine preference first two puffs | .404 | .782 |
| (8) Nicotine preference last two puffs | −.528 | .738 |

TABLE I-continued

Principal Components Analysis of Smoking Variables

Rotated Factor Loadings

| Variable | Factor 1 (smoke) Eigenvalue = 3.76 | Factor 2 (Nicotine) Eigenvalue = 2.97 |
|---|---|---|
| puffs | | |

Blood nicotine levels were estimated from saliva levels as described above. A paired t-test comparison between placebo and 8 mg transdermal nicotine conditions confirmed that there were significantly higher nicotine levels of the 8 mg cigarettes (10 ng/ml vs 16 ng/ml, $p<0.01$). Thus, at least some nicotine was absorbed from the transdermal patch.

A 2(Nicotine Dose)×4(Time) ANOVA showed that heart rate declined steadily with time ($p<0.00001$) but was not affected by transdermal nicotine ($p>0.5$). A 2(Nicotine Dose)×2(Mixer) ANOVA on the change in heart rate after each smoking period showed that heart rate increased after Mixer 2, following 90 minutes deprivation, more than after the first smoking period in each session ($p<0.05$ for the main effect of Mixer). A t-test for the mean heart rate change after Mixer 1 indicated that the first smoking period did not increase heart rate ($p>0.2$). In contrast, the mean heart rate increase after Mixer 2 was significant ($p<0.05$).

Subjects' responses to the questionaire asking whether they believed they had received nicotine on each day were scored and responses were counted as correct if subjects stated nicotine was received in the 8 mg transdermal nicotine condition and not with the placebo. Only four of the ten subjects guessed correctly on both days, and assuming the probability of success was 0.25 for random guessing, the probability of the observed level of performance or better was 0.22. Thus, the subjects' ability to accurately discriminate between the placebo and 8 mg nicotine conditions was not significanly better than chance.

The results supported the hypothesis that transdermal nicotine would prevent the increase in craving for cigarettes during a short (90 min) deprivation period. Moreover, nicotine preference during the initial puffs of the subsequent smoking period was also diminished by transdermal nicotine. Despite the influence of transdermal nicotine in this experiment, subjects generally were not able to discriminate whether they had received nicotine or placebo. These findings support the claim that transdermal nicotine promotes smoking cessation.

EXAMPLE VII

A test was conducted to determine the acceptability of a low-dose aerosol spray for use with cigarettes smokers. Two adult male smokers who consume a pack per day of cigarettes participated in the study.

The smokers were presented with test puffs of aerosols containing either 0.01%, 0.1% or 1% nicotine base in aqueous solution. An ultrasonic nebulizer was used to generate aerosols with small droplet sizes, and the aerosol was allowed to settle for approximately five seconds before each inhalation to remove droplets larger than approximately 10 microns. During the settling period the aerosol was contained in a length of Teflon tubing (¼ inch diameter) approximaely 2 meters in length. An allowed subjects to puff on the opposite end of the tube and feel a draw resistance comparable to that of a cigarette.

The results suggest that a 1% nicotine solution was perceived as moderately satisfying the urge to smoke.

The results of the testing are shown in the accompanying composite of FIG. 5 which show the satisfaction, the harshness, the strength, the likeness or pleasure and the similarity with respect to cigarettes for nicotine levels of 0.01%, 0.1%. It can be observed that preferences and in each case the satisfaction and harshness and strength and similarity to cigarettes increased proportionally with the percentage increase in nicotine.

EXAMPLE VIII

One subject was given eight mg of transdermal nicotine applied under a polyethylene patch. Thirty minutes later the subject received puffs of a 1% nicotine aerosol delivered through an ultrasonic nebulizer. One puff was taken every 45 seconds for a five minute period. Fifteen minutes later a second set of puffs was taken for five minutes. Reports of cigarette craving were gathered at the beginning of the session, at which time the subject had abstained from smoking from two hours perviously, and again before and after each set of nicotine puffs. Within one hour after application of the transdermal nicotine patch and subsequent puffs of nicotine aerosol, reported craving for cigarettes was reduced.

A plot of the craving on a scale of one to five, as a function of time, was made. After thirty minutes from the application of the transdermal patch, the first set of puffs were taken and then reduced craving one full point. After about fifteen minutes when craving increased about one point to the original level which was obtained after application of the patch, the second set of puffs of aerosol were taken and reduced the craving about one full point back to the same level achieved after the the initial set of puffs. This demonstrates that the combination of transdermally applied nicotine and the nicotine aerosol spray can be effective in reducing craving for tobacco smoking.

EXAMPLE IX

Ten subjects are given 8 mg transdermal nicotine under polyethylene patches. The subjects abstained from smoking for two hours previously. Thirty minutes later the subjects receive puffs of a 1% nicotine aerosol through an ultrasonic nebulizer. One puff is taken every 45 seconds for a five minute period. Fifteen minutes later a second set of puffs is taken for five minutes. Reports of craving are again taken before and after each set of nicotine puffs. Within one hour after application of the transdermal nicotine patch and subsequent puffs of nicotine aerosol, reported craving for cigarettes is reduced.

A plot of the average craving for the ten subjects on a scale of from one to ten, as a function of time, is then made. After thirty minutes from the application of the transdermal patch, the first set of puffs are taken and these reduce cravings an average of approximately one point. After about fifteen minutes when craving increases an average of about one point to the original level which was obtained after application of the patch the second set of puffs of aerosol are taken and reduced the craving about one full point back to the same level achieved after the initial set of puffs. This also demonstrates that the combination of transdermally applied nicotine and the nicotine aerosol spray can be effective in reducing craving for tobacco smoking.

Thus there has been described a unique and novel method and apparatus which enables the effective reduction in the incidence of tobacco smoking and the attendant reduction, if not elimination, of dependency on tobacco smoking without relapse and return to the dependency. It should be understood that many changes, modifications, variations and other uses and applications will become apparent to those skilled in the art after considering this specification. Therefore, any and all such changes, modifications, variations and other uses and applications which may become apparent to those skilled in the art after considering this specification are deemed to be covered by the invention.

Having thus described my invention what I desire to claim and secure by Letters Patent is:

1. A method of aiding in the reduction of incidence of tobacco smoking, said method comprising:
    (a) applying a patch containing nicotine to the skin of a person with whom smoking reduction is desired,
    (b) allowing the nicotine in the patch to transdermally migrate into the person's bloodstream to achieve a desired systemic nicotine level,
    (c) administering a nicotine containing aerosol spray to the oral cavity of the user to provide the desired sensation in the respiratory tract to which the user is accustomed from normal tobacco smoking, thereby providing the user with desired systemiic nicotine levels and the sensation of smoking without most of the other harmful effects of smoking.

2. The method of claim 1 further characterized in that said method comprises providing nicotine in the patch so that transdermal migration into the bloodstream is at a rate sufficient to correspond to the nicotine level in the blood achieved by normal smoking patterns of the user.

3. The method of claim 2 further characterized in that the method comprises measuring the nicotine levels in the bloodstream approximating those at the varying spaced apart time measurements.

4. The method of claim 2 further characterized in that said method comprises applying the patch at periodic time intervals to generally correspond with a user's smoking patterns.

5. The method of claim 1 further characterized in that the method comprises measuring the nicotine level in the person's bloodstream and controlling the amount of nicotine applied to the patch to achieve a certain relatively constant nicotine level in the blood over a specified period of time.

6. The method of claim 1 further characterized in that said aerosol spray hs droplets between about 1 micron to about 10 microns in diameter and with size selected to stimulate either the upper respiratory region or the lower respiratory region or both.

7. The method of claim 6 further characterized in that the aerosol spray contains nicotine in an amount to render about 0.005 mg to about 0.03 mg per inhalation.

8. The method of claim 6 further characterized in that said method comprises administering the aerosol spray having droplets within a size range of about 1 micron to about 5 microns for stimulating the lower respiratory regions of a user.

9. The method of claim 6 further characterized in that said method comprises administering the aerosol spray having droplets with a size range of about 5 microns to about 10 microns for stimulating the upper respiratory regions of a user.

10. The method of claim 6 further characterized in that said method comprises administering an aerosol spray having a nicotine content from about 0.008 mg per inhalation to about 0.15 mg per inhalation.

11. A spray and transdermal patch combination for aiding in the reduction of incidence of tobacco smoking by administration of nicotine in a manner which minimizes harmful side effects of nicotine administration, said combination comprising:
(a) an occlusive patch for application to the skin of a person with whom smoking reduction is desired,
(b) a selected amount of nicotine in the patch which is allowed to transdermally migrate from the patch into the person's bloodstream to achieve a desired systemic nicotine level, and
(c) a nicotine containing aerosol spray for delivery of an aerosol to the oral cavity of the user simultaneously with the application of nicotine from the patch, the amount of nicotine contained in the patch and thereby delivered from the patch being generally inversely related to the amount of nicotine normally delivered from the spray but which is still present in an amount to provide the desired sensation in the respiratory tract to which the user is accustomed from normal tobacco smoking and to permit peak levels of nicotine in the bloodstream upon demand by a user, thereby providing the user with desired systemic nicotine levels and the sensation of smoking without most of the other harmful effects of smoking.

12. The combination of claim 11 further characterized in that said combination comprises a selected amount of nicotine in the patch sufficient to maintain transdermal migration into the bloodstream at a rate sufficient to correspond to the nicotine level in the blood achieved by normal smoking patterns of the user.

13. The combination of claim 11 further characterized in that said patch comprises at least 8 milligrams of nicotine therein.

14. The combination of claim 11 further characterized in that said patch comprises about 1 to about 5 milligrams of nicotine and said patch also comprises a penetration enhancer.

15. The combination of claim 11 further characterized in that said patch comprises a sufficient amount of nicotine to be delivered at a rate to produce a level of about 10 nanograms of nicotine per milliliter of blood at the start of a smoking reduction program.

16. The combination of claim 11 further characterized in that said patch comprises a sufficient amount of nicotine in the patch and is constructed to transdermally administer the nicotine from the patch to maintain about 50 to about 250 micrograms of nicotine in the user's bloodstream.

17. The combination of claim 11 further characterized in that the pH of the nicotine and any carrier therefore in the patch is maintained between 7 and 9.

18. The combination of claim 11 further characterized in that said aerosol spray has droplets between about 1 micron to about 10 microns in diameter and with size selected to stimulate either the upper respiratory region or the lower respiratory region or both.

19. The combination of claim 11 further characterized in that the aerosol spray contains nicotine in an amount to render about 0.005 mg to about 0.03 mg per inhalation.

20. The combination of claim 11 further characterized in that said aerosol spray has droplets within a size range of about 1 micron to about 5 microns for stimulating the lower respiratory regions of a user.

21. The combination of claim 11 further characterized in that said aerosol spray has droplets within a size range of about 5 microns to about 10 microns for stimulating the upper respiratory regions of a user.

22. The combination of claim 11 further characterized in that said aerosol spray has a nicotine content sufficient to provide from about 0.008 mg per inhalation to about 0.015 mg per inhalation.

23. A spray and transdermal patch combination for aiding in the reduction of incidence of tobacco smoking by administration of nicotine in a manner which minimizes harmful side effects of nicotine administration, said combination comprising:
(a) an occlusive patch for application to the skin of a person with whom smoking reduction is desired,
(b) a selected amount of nicotine in the patch which is allowed to transdermally migrate from the patch into the person's bloodstream to achieve a desired systemic nicotine level, and
(c) a nicotine containing aerosol spray for delivery of an aerosol to the oral cavity of the user, the amount of nicotine being deliverable with each spray being substantially less than the amount of nicotine deliverable from a puff of tobacco smoke and generally in an amount insufficient to provide any substantial level of nicotine but nevertheless present in an amount to provide the desired sensation in the respiratory tract to which the user is accustomed from normal tobacco smoking and to permit peak levels of nicotine in the bloodstream upon demand by a user, the combination of the patch and spray thereby providing the user with desired systemic nicotine levels and the sensation of smoking without most of the other harmful effects of smoking.

24. The combination of claim 23 further characterized in that said aerosol spray has droplets between about 1 micron to about 10 microns in diameter and with size selected to stimulate either the upper respiratory region or the lower respiratory region or both.

25. The combination of claim 23 further characterized in that the aerosol spray contains nicotine in an amount to render about 0.005 mg to about 0.03 mg per inhalation.

26. The combination of claim 23 further characterized in that said aerosol spray has a nicotine content sufficient to provide from about 0.008 mg per inhalation to about 0.015 mg per inhalation.

27. The combination of claim 23 further characterized in that the amount of nicotine in the nicotine containing aerosol spray for delivery to the oral cavity being delivered simultaneously with the application of nicotine from the patch, the amount of nicotine delivered from the patch being generally inversely related to the amount of nicotine normally delivered from the spray but which is still present in an amount to provide the desired sensation in the respiratory tract to which the user is accustomed from normal tobacco smoking and to permit peak levels of nicotine in the bloodstream upon demand by a user.

28. A spray and transdermal patch combination for aiding in the reduction of incidence of tobacco smoking by administration of nicotine in a manner which minimizes harmful side effects of nicotine administration, said combination comprising:
(a) an occlusive patch for application to the skin of a person with whom smoking reduction is desired,
(b) a selected amount of nicotine in the patch which is allowed to transdermally migrate from the patch into the person's bloodstream to achieve a desired systemic nicotine level, (c) a nicotine antagonist in said patch which is allowed to migrate from the patch into a users skin to reduce peripheral side effects of the nicotine, and (d) a nicotine containing aerosol spray for delivery of an aerosol to the oral cavity of the user to provide the desired sensation in the respiratory tract to which the user is accustomed from normal tobacco smoking and to permit peak levels of nicotine in the bloodstream upon demand by a user, thereby providing the user with desired systemic nicotine levels and the sensation of smoking without most of the other harmful effects of smoking.

29. The combination of claim 28 characterized in that the nicotine antagonist is hexamethonium.

* * * * *